United States Patent

Wolter et al.

[11] Patent Number: 5,792,881
[45] Date of Patent: Aug. 11, 1998

[54] THIOLSILANES, METHOD OF THEIR PRODUCTION AND OF THEIR USE

[75] Inventors: Herbert Wolter, Grossrinderfeld; Werner Storch, Hoechberg, both of Germany

[73] Assignee: Fraunhofer-Gesellschaft zur Förderung der angewandten Forschung e.V., Munich, Germany

[21] Appl. No.: 793,270

[22] PCT Filed: Jul. 5, 1996

[86] PCT No.: PCT/DE96/01217

§ 371 Date: Mar. 5, 1997

§ 102(e) Date: Mar. 5, 1997

[87] PCT Pub. No.: WO97/02270

PCT Pub. Date: Jan. 23, 1997

[30] Foreign Application Priority Data

Jul. 6, 1995 [DE] Germany ............ 195 24 657.8

[51] Int. Cl.[6] .................. C07F 7/10; C07F 7/08; C07F 7/18
[52] U.S. Cl. .................. 556/429; 556/419; 556/428; 556/420; 556/402; 556/404; 556/405; 556/9; 556/10; 556/12; 534/11; 534/15
[58] Field of Search .................. 556/419, 429, 556/428, 420, 402, 404, 405, 9, 10, 12; 534/15, 11

[56] References Cited

U.S. PATENT DOCUMENTS 4,997,965 3/1991 Lohmann et al. .............. 556/419

*Primary Examiner*—Paul F. Shaver
*Attorney, Agent, or Firm*—Karl Hormann

[57] ABSTRACT

The invention relates to hydrolyzable and polyadditive silanes, a method of their production and of their use in the production of (hetero) silicic acid polycondensates and of polyadducts. The silanes in accordance with the invention have the general formula $$[(HS-R^5)_n R^6-S-E-R^5]_a SiX_x R^3_{4-a-x} \qquad (I)$$

in which the groups and indices are equal or different and have the following meaning:

$E = -CO-NH-$, $CS-NH-$, $-CH_2-CH_2-$ or $-CH_2-CH(OH)-$;

$R^3$ = alkyl, alkenyl, aryl, alkylaryl or arylalkyl each with 1 to 15 carbon atoms, whereby these groups may be interrupted by oxygen or sulfur atoms, by ester, carbonyl, amide or amino groups;

$R^5$ = Alkene, arylene, arylenealkene or arylenealkene each with 1 to 15 carbon atoms, whereby these groups may be interrupted by oxygen or sulfur atoms, by ester, carbonyl, amide or amino groups;

$R^6$ = alkene, arylene, arylenealkene or arylenealkene each with 1 to 15 carbon atoms, whereby these groups may be interrupted by oxygen or sulfur atoms, by ester, carbonyl, amide or amino groups;

X = hydrogen, halogen, hydroxy, alkoxy, acyloxy, alkylcarbonyl, alkoxycarbonyl or $NR''_2$;

a = 1, 2 or 3;
n = 2, 3, 4 or 5;
x = 1, 2 or 3.

4 Claims, No Drawings

THIOLSILANES, METHOD OF THEIR PRODUCTION AND OF THEIR USE

TECHNICAL FIELD

The invention relates to hydrolyzable and polyadditive silanes, a method of their production and their use in the production of organically modified silicic acid polycondensates or hetero silicic acid polycondensates, as well as in the production of macromolecular materials by polyaddition.

THE STATE OF THE ART

Hydrolyzable, organically modified silanes are widely used in the manufacture of scratch-proof substrates, for the production of filler, of adhesives and caulking compounds or of molded articles. To these ends, the silanes are hydrolytically condensed, either by themselves, in mixtures with or in the presence of further hydrolyzable and/or condensible components, their final curing being accomplished thermically, photochemically or by redox induction.

Thus, scratch-proof coatings are known, for instance, from German Patent specification 3,407,087 C2 which are made by hydrolytically condensing a mixture, which, among others, consists of a hydrolyzable titanium or zirconium compound and of a hydrolyzable organofunctional silane $R_m(R"Y)_n SiX_{(4-m-n)}$, wherein R' is an alkyl or alkenyl, for instance, R" is an alkene or alkenylene and X represents a hydrolyzable group.

Adhesive and caulking compounds are known, for instance, from German Patent specification DE 3,536,716 A1, which have been made by hydrolytically condensing one or more organosilanes of the general formula $R_m SiX_{4-m}$ and, if required, one or more components $SiX_4$ and/or $R_n(R"Y)_p SiX_{4-n-p}$, wherein R and R" are, for instance, alkyl, alkenyl, aryl, alkylaryl, arylalkyl, alkenylaryl or arylalkenyl, X is, for instance, hydrogen, halogen, hydroxy, alkoxy or acyloxy, and Y is, for instance, a halogen or a, if required, substituted amino, amide, aldehyde, alkylcarbonyl, carboxy, hydroxy, mercapto or cyano group.

Furthermore, commercial silanes with reactive double bonds are known, such as, for instance, (meth)acryloxysilanes of the following type,

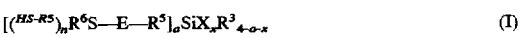

wherein R is hydrogen or methyl and X is, for instance, halogen or alkoxy. These silanes are hydrolyzable and polymerizable and may be used in the production of the systems mentioned above. They offer the great advantage that the resulting coating, the resulting filler, adhesive or caulking compound or the resulting molded article may be cured thermically, photochemically or by redox induction by polymerization at the reactive double bonds.

In general, commercial silanes with reactive double bonds, such as, for instance, the above mentioned (meth)acryloxysilanes constitute monofunctional compounds with one C=C double bond, and, as a rule, low molecular and prior to their Si—X-hydrolysis and condensation they are thus relatively volatile compounds which because of inherent acrylic group give are toxicologically apprehensible. During further processing by polymerization or modified functionalization, these silanes are additionally disadvantageous that because of the presence of only one reactive C=C double bond only chain polymers can be obtained and that with prior functionalization the C=C double bond necessary for the organic polymerization is usually lost. Furthermore, usually only a short chain is provided between the double bond and the silicon capable of forming an anorganic network, so that by way of the organic groups the mechanical properties (flexibility etc.) may be varied within narrow limits only.

While hydrolyzable and polymerizable silanes provided with more than one reactive C=C double bond and in which the spacing between the reactive double bond and the silicon capable of forming an organic network is larger are known from German Patent specification DE 4,011,044, the need for improvement remains nevertheless, including as regards a functionalization of the molecule.

It is, therefore, the task of the present invention to provide novel organically modified silanes which are hydrolyzable and polyadditive, which by themselves, in mixtures or together with other hydrolyzable, condensible or polyadditive components may be processed into scratch-proof coatings, into filling, adhesive or caulking compounds, into molded articles, foils or fibers, into fillers or embedding materials. These silanes are to be universally applicable and they are to be incorporable into an anorganic-organic composite system, i.e., into an anorganic-organic network. Moreover, these silanes are to be producible quickly and simply, i.e., without an elaborate synthesizing process.

DESCRIPTION OF THE INVENTION

This task is accomplished by silanes having at least two thiol groups and corresponding to the general formula I.

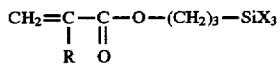  (I)

The groups of the general formula are equal or different and have the following meaning:

E=—CO—NH—, CS—NH—, —CH$_2$—CH$_2$— or —CH$_2$—CH(OH)—;

R$^3$=alkyl, alkenyl, aryl, alkylaryl or arylalkyl each with 1 to 15 carbon atoms, whereby these groups may be interrupted by oxygen or sulfur atoms, by ester, carbonyl, amide or amino groups;

R$^5$=Alkene, arylene, arylenealkene or alkenearylene each with 1 to 15 carbon atoms, whereby these groups may be interrupted by oxygen or sulfur atoms, by ester, carbonyl, amide or amino groups;

R$^6$=alkene, arylene, arylenealkene or alkenearylene each with 1 to 15 carbon atoms, whereby these groups may be interrupted by oxygen or sulfur atoms, by ester, carbonyl, amide or amino groups;

X=hydrogen, halogen, hydroxy, alkoxy, acyloxy, alkylcarbonyl, alkoxycarbonyl or NR"$_2$;

a=1, 2 or 3;

n=2, 3, 4 or 5;

x=1, 2 or 3.

The alkyl groups are, for instance, straight-chain, crosslinked or cyclic groups with 1 to 15, more particularly 1 to 10 carbon atoms and preferably low alkyl groups with 1 to 6, particularly preferred 1 to 4 carbon atoms. Particular examples are methyl, ethyl, n-propyl, i-propyl, n-butyl, i-butyl, s-butyl, t-butyl, n-pentyl, h-hexyl, cyclohexyl, 2-ethylhexyl, dodecyl and octadecyl.

The alkenyl groups are, for instance, straight-chain, crosslinked or cyclic groups with 2 to 15, preferably 2 to 10 carbon atoms and preferably low alkenyl groups with 2 to 6 carbon atoms, such as, for instance, vinyl, allyl and 2-butenyl.

Preferred aryl groups are phenyl, biphenyl and naphthyl;. The alkoxy, acyloxy alkylamino, dialkylamino, alkylcarbonyl, alkoxycarbonyl, arylalkyl, alkylaryl, alkene and alkenearylene groups are preferably derived from the above-mentioned alkyl and aryl groups. Particular examples are methoxy, ethoxy, n- and I-propoxy, n-, i-, s- and t-butoxy, monomethylamino, monoethylamino, dimethylamino, diethylamino, N-ethylanilino, acetyloxy, propionyloxy, methylcarbonyl, ethylcarbonyl, methoxycarbonyl, ethoxycarbonyl, benzyl, 2-phenylethyl and tolyl.

The mentioned groups may, if required, carry one or more substituents, such as e.g., halogen, alkyl, hydroxyalkyl, alkoxy, aryl, aryloxy, alkylcarbonyl, alkoxycarbonyl, furfuryl, tetrahydrofurfuryl, amino, monoalkylamino, dialkylamino, trialkylammonium, amido, hydroxy, formyl, carboxy, mercapto, cyano, isocyanato, nitro, epoxy, $SO_3H$ or $PO_4H_2$.

Among the halogens, fluorine, chlorine and bromine, and especially chlorine, are preferred.

Where a or $x \geq 2$ the groups X, $R^3$, $R^5$, and $R^6$ may each be of the same or different meaning.

Such "oligothiolsilanes" are not known in the state of the art and are particularly well suited for theol.-en-additions. The silanes of the general formula I are hydrolytically condensible by way of their X groups and (poly)additive by way of their theol. groups. They are incorporable by hydrolytic condensation into an anorganic network and by polyaddition into an organic network. The silanes of general formula I may by themselves or together with other cocondensible components and by conventional methods such as, for instance, a sol-gel process, be processed into (hetero) silicic acid polycondensates which thereafter may be cross-linked by polyaddition (e.g. a thiol-en-addition). But the silanes of general formula I may be polyaddition, e.g. a thiol-en-addition, be process into polyadducts which may subsequently be cured further by hydrolytic condensation.

For forming the anorganic network, the silanes in accordance with the invention or the product of the polyaddition of the silanes in accordance with the invention are hydrolyzed and polycondensed, if required by adding other cocondensible components. Preferably, the polycondensation is performed by the sol-gel-process, as described, e.g., in German Patent specifications DE A1 2,758,414; 2,758,415; 3,011,76; 3,826,715 and 3,835,968.

For forming the organic network, the silanes in accordance with the invention or the polycondensate of the silanes in accordance with the invention are subjected to polyaddition, if required by adding other polyadditive components.

The silanes in accordance with the invention may be converted into macromolecular materials by polyaddition, for instance to components having one or more C=C double bonds (theol.-en-addition). Similarly, it is possible to perform the polyaddition following the hydrolytic condensation of the silanes in accordance with the invention. If the olefine to be added contains at least two C=C double bonds, it is possible to form a multi-dimensional organic network. If hydrolyzable silanes with at least one C=C double bond are used for the polyaddition a multi-dimensional network will be formed if only one C=C double bond is provided in the en-silane.

The general reaction pattern has the following appearance:

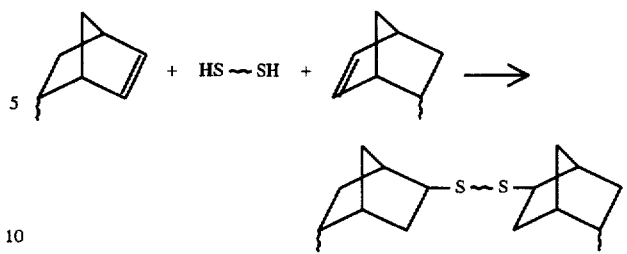

It has surprisingly been found that silanes of general formula I are particularly well suited for cross-linking of silanes of general formula II or of polycondensates from silanes of general formula II.

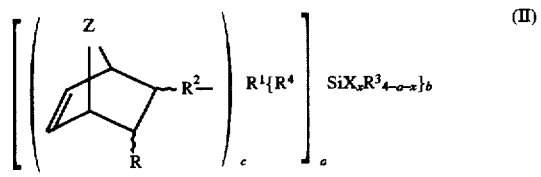

The groups and indices of general formula II have the following meaning:

R=Hydrogen, $R^2$—$R^1R^4SiX_xR^3_{3-x}$, carboxyl, alkyl, alkenyl, aryl, alkylaryl or arylalkyl each with 1 to 15 carbon atoms, whereby the groups may be interrupted by oxygen or sulfur atoms, by esters, carbonyl, amide or amino groups;

$R^1$=alkene, arylene, arylenealkene or alkenearylene each with 0 to 15 carbon atoms, whereby these groups may be interrupted by oxygen or sulfur atoms, by ester, carbonyl, amide or amino groups;

$R^2$=Alkene, arylene, arylenealkene or alkenearylene each with 0 to 15 carbon atoms, whereby these groups may be interrupted by oxygen or sulfur atoms, by ester, carbonyl, amide or amino groups;

$R^3$=alkyl, alkene, aryl, alkylaryl or arylalkyl each with 1 to 15 carbon atoms, whereby these groups may be interrupted by oxygen or sulfur atoms, by ester carbonyl, amide or amino groups;

$R^4$=—$(CHR^6$—$CHR^6)_n$—, with n=01 or 1, —$CHR^6$—$CHR^6$—S—$R^5$—, —CO—S—$R^5$—, $CHR^6$—$CHR^6$—$NR^6$—$R^5$—, —S—$R^5$—, —Y—CO—NH—$R^5$—, —CO—O—$R^5$—, —Y—CO—$C_2H_3$(COOH)—$R^5$—, —Y—CO—$C_2$—$H_3$(OH)—$R^5$— or —CO—$NR^6$—$R^5$—;

$R^5$=alkene, arylene, arylenealkene or alkenearylene each with 1 to 15 carbon atoms, whereby these groups may be interrupted by oxygen or sulfur atoms, by ester, carbonyl, amide or amino groups;

$R^6$=hydrogen, alkyl or aryl with 1 to 10 carbon atoms;

X=hydrogen, halogen, hydroxy, alkoxy, acyloxy, alkylcarbonyl, alkoxycarbonyl or $NR"_2$, with R"=hydrogen, alkyl or aryl;

Y=—O—, —S— or $NR^6$;

Z=—O— or —$(CHR^6)_m$—, with m=1 or 2;

a=1, 2 or 3, with b=1 for a=2 or 3;

b=1, 2 or 3, with a=1 for b=2 or 3;

c=1 to 6;

x=1, 2 or 3;

a+x=2, 3 or 4.

The silanes of formula II are polyaddible by way of the C=C double bonds of the norbornene, oxabicycloheptene or bicyclooctene groups, for instance onto thiols and ring-scission polymerizable, and by way of the X groups they are hydrolyzable. An anorganic network having Si—O—Si units may be formed by way of the hydrolyzable groups, whereas the C=C double bonds contained in the bicyclic groups may be subjected to polymerization or polyaddition, forming an organic network at the same time.

The formation of a three-dimensional organic network is possible if two or more bicyclic groups are present. The mechanical properties (e.g. flexibility) and the physico-chemical properties (adsorption, refractive index, adhesion, etc.) of the (hetero)polycondensates may be influenced and adjusted to given applications by the spacing between the Si atom and the bicyclic group, i.e. by way of the length of the chain, and by way of the presence of further functional groups in this chain. The aliphatic groups result in flexible and the aromatic groups result in rigid products. The cross-linkage density is adjustable by way of the number of groups capable of cross-linking (Sh groups and, e.g., norbornene groups). The cross-linkage density in turn affects the properties and, hence, the possibilities of use of the (hetero) polycondensates.

Properties resembling silicon or glass of the (hetero) polycondensates may be adjusted by the structure of an anorganic network depending upon the kind and number of the hydrolyzable groups.

If the possibilities of variation of the cocondensible and copolymerizable or coadditive components are taken into consideration, it will become apparent through the silanes in accordance with the invention (hetero) silicic acid polycondensates are provided which may be adjusted to many given fields of use in many different ways and which for this reason may be used in all areas in which (hetero) silicic acid polycondensates have hitherto been used, but which also open new possibilities of use, as, for instance, in the fields of optics, electronics, medicine, opto-electronics as well as in the food packaging industry.

The silanes in accordance with the invention or their polycondensates or polyadducts may either be used as such or in compounds which additionally include additives adjusted to a given purpose, e.g., conventional lacquer additives, solvents, fillers, photo initiators, thermic initiators, flow agents and pigments. The silanes in accordance with the invention or the silane-containing compounds are suitable, for instance, for the production of coating, filling and bulk materials, of adhesives and injection molding materials, of fibers, particles, foils, bonding initiators, impression forming materials and of embedding materials. Coatings and molded articles made of silanes in accordance with the invention offer the advantage of being photochemically structurable. Specific fields of application are, for instance, the coating of substrates of metal, plastic, paper, ceramic, etc. by submersion, pouring, brushing, spraying, electrostatic spraying, galvanic lacquering etc., their use for optical, opto-electrical and electronic components, the production of fillers, fibers or foils, the production of scratch-proof and/or abrasion-resistant anti-corrosion coatings, the manufacture of molded articles, for instance by injection molding, die casting, pressing, rapid prototyping or extrusion, the manufacture of (contact)lenses and the production of composites, e.g. including fibers, fillers or woven webs.

Ways of Practicing the Invention

The silanes of general formula I may be obtained on the basis of the following reaction pattern. To this end, oligothiols are added to silanes the organic group or groups of which contain isocyanate, thioisocyanate or epoxy groups or C=C double bonds. Such silanes are commercially available, or they may be produced by methods described in "Chemie und Technologie der Silicone" (W. Noll, Verlag Chemie GmbH. Weinheim/Bergstrasse, Germany, 1968).

$a(HS-R^5)_nR^6-SH+[OCN-R^5]_aSiX_xR^3_{4-a-x} \rightarrow \ldots$ $\ldots \rightarrow [(HS-R^5)_nR^6-S-CO-NH-R^5]_aSiX_xR^3_{4-a-x}$ $a(HS-R^5)_nR^6-SH+[SCN-R^5]_aSiX_xR^3_{4-a-x} \rightarrow \ldots$ $\ldots \rightarrow [(HS-R^5)_nR^6-S-CS-NH-R^5]_aSiX_xR^3_{4-a-x}$ $a(HS-R^5)_nR^6-SH+[H_2C-O-CH-R^5]_aSiX_xR^3_{4-a-x} \rightarrow$ $\ldots \rightarrow [(HS-R^5)_nR^6-S-CH_2-CH(OH)-R^5]_aSiX_xR^3_{4-a-x}$ $a(HS-R^5)_nR^6-SH+[H_2C=CH-R^5]_aSiX_xR^3_{4-a-x} \rightarrow \ldots$ $\ldots \rightarrow [(HS-R^5)_nR^6-S-CH_2-CH_2-R^5]_aSiX_xR^3_{4-a-x}$ The following, without restriction of generality, represents a concrete example:

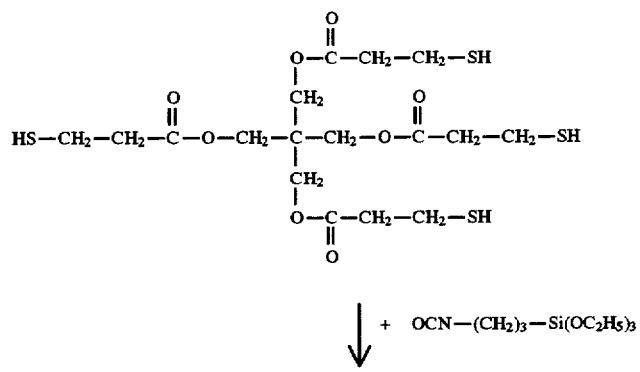

-continued

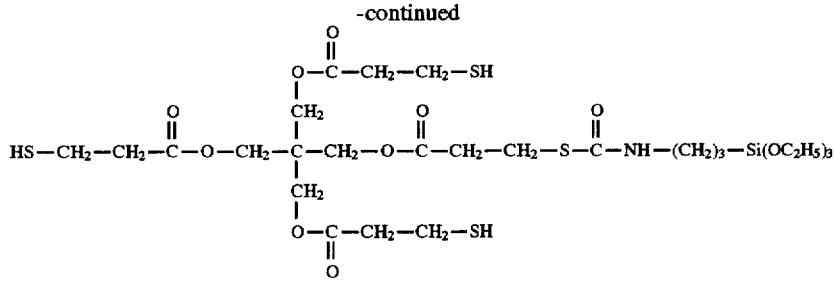

We claim:

1. Silanes of the general formula I,

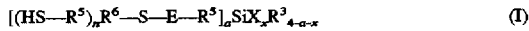

in which the groups and indices are equal or different and have the following meaning:

E=—CO—NH—, CS—NH—, —CH$_2$—CH$_2$— or —CH$_2$—CH(OH)—;

R$^3$=alkyl, alkenyl, aryl, alkylaryl or arylalkyl each with 1 to 15 carbon atoms, whereby these groups may be interrupted by oxygen or sulfur atoms, by ester, carbonyl, amide or amino groups;

R$^5$=Alkene, arylene, arylenealkene or alkenearylene each with 1 to 15 carbon atoms, whereby these groups may be interrupted by oxygen or sulfur atoms, by ester, carbonyl, amide or amino groups;

R$^6$=alkene, arylene, arylenealkene or alkenearylene each with 1 to 15 carbon atoms, whereby these groups may be interrupted by oxygen or sulfur atoms, by ester, carbonyl, amide or amino groups;

X=hydrogen, halogen, hydroxy, alkoxy, acyloxy, alkylcarbonyl, alkoxycarbonyl or NR''$_2$;

a=1, 2 or 3;

n=2, 3, 4 or 5;

x=1, 2 or 3.

2. A method of making silanes of the kind defined in claim 1, characterized by the fact that oligothiols of the general formula (HS—R$^5$)$_n$R$^6$—SH are added to silanes of the general formula [H$_2$C—O—CH—R$^5$]$_a$SiX$_x$R$^3$$_{4-a-x}$, [CH$_2$=CH—R$^5$]$_a$SiX$_x$R$^3$$_{4-a-x}$, [OCN—R$^5$]$_a$SiX$_x$R$^3$$_{4-a-x}$, or [SCN—R$^5$]$_a$SiXxR$^3$$_{4-a-x}$, whereby the groups and indices are equal or different and have the meaning defined in claim 1.

3. The method of claim 2, including the step of a thiol-en addition.

4. The method of making, with silanes of the kind defined in claim 1, one of organically modified silicic acid polycondensates and organically modified hetero silicic acid polycondensates by hydrolytic condensation of at least one hydrolytically condensible compound of the silicon and at least one of an element from the group of B, Al, P, Sn, Pb, the transitional metals, of the lanthanides and the actinides and a precondensate derived from said compounds in the presence of at least one of a catalyst and a solvent, by the effect of water whereby 5–100 mol-% are selected on the basis of monomeric compounds of the hydrolytically condensible compounds of silicones of the general formula I

in which the groups and indices are as defined in claim 1.

* * * * *